US010556068B2

(12) United States Patent
Glover et al.

(10) Patent No.: US 10,556,068 B2
(45) Date of Patent: Feb. 11, 2020

(54) INJECTION DEVICE

(71) Applicant: CONSORT MEDICAL PLC, Hemel Hempstead (GB)

(72) Inventors: Robert Glover, Derbyshire (GB); Alastair Willoughby, Cambridgeshire (GB); Brad Howarth, Cambridgeshire (GB)

(73) Assignee: Consort Medical PLC, Hemel Hempstead (GB)

( * ) Notice: Subject to any disclaimer, the term of this patent is extended or adjusted under 35 U.S.C. 154(b) by 148 days.

(21) Appl. No.: 15/759,642

(22) PCT Filed: Aug. 19, 2016

(86) PCT No.: PCT/GB2016/052569
§ 371 (c)(1),
(2) Date: Mar. 13, 2018

(87) PCT Pub. No.: WO2017/046556
PCT Pub. Date: Mar. 23, 2017

(65) Prior Publication Data
US 2019/0046737 A1 Feb. 14, 2019

(30) Foreign Application Priority Data

Sep. 14, 2015 (GB) .................................. 1516219.1

(51) Int. Cl.
*A61M 5/32* (2006.01)
*A61M 5/20* (2006.01)
*A61M 5/50* (2006.01)

(52) U.S. Cl.
CPC .......... *A61M 5/326* (2013.01); *A61M 5/3245* (2013.01); *A61M 5/2046* (2013.01);
(Continued)

(58) Field of Classification Search
CPC .. A61M 5/326; A61M 5/3245; A61M 5/3243; A61M 5/3232; A61M 5/3271;
(Continued)

(56) References Cited

U.S. PATENT DOCUMENTS

| 2003/0060776 A1* | 3/2003 | Heiniger | A61M 5/326 |
| | | | 604/198 |
| 2003/0078546 A1* | 4/2003 | Jensen | A61M 5/3202 |
| | | | 604/232 |
| 2006/0178639 A1 | 8/2006 | Eric et al. | |

FOREIGN PATENT DOCUMENTS

| DE | 102006029911 A1 | 1/2008 |
| EP | 1949929 A1 | 7/2008 |
| WO | 9220390 A1 | 11/1992 |

OTHER PUBLICATIONS

International Preliminary Report on Patentability dated Mar. 20, 2018, for corresponding International Application No. PCT/GB2016/052569; International Filing Date: Aug. 19, 2016 consisting of 7-pages.

(Continued)

*Primary Examiner* — Bhisma Mehta
*Assistant Examiner* — Nilay J Shah
(74) *Attorney, Agent, or Firm* — Christopher & Weisberg, P.A.

(57) ABSTRACT

An injection device having an outer housing configured to receive a syringe. The syringe has a barrel for containing medicament and a needle in fluid communication with the barrel. The device further has a needle shield axially moveable relative to the outer housing between a needle covering position and a needle exposing position and a helical compression spring to bias the needle shield axially forwardly toward the needle covering position. A locking sleeve, axially movable relative to the outer housing between a non-locking position and a locking position, selectively (Continued)

limits axial movement of the needle shield. In a first configuration, the needle shield is axially slideable within the locking sleeve to permit rearward axial movement of the needle shield from the needle covering position to the needle exposing position.

23 Claims, 6 Drawing Sheets

(52) U.S. Cl.
 CPC ......... *A61M 5/3232* (2013.01); *A61M 5/3243* (2013.01); *A61M 5/3271* (2013.01); *A61M 5/50* (2013.01); *A61M 2005/3247* (2013.01); *A61M 2005/3267* (2013.01)

(58) Field of Classification Search
 CPC ........ A61M 5/50; A61M 5/3257; A61M 5/20; A61M 5/2033; A61M 5/2046; A61M 2005/325; A61M 2005/3254; A61M 2005/3247; A61M 2005/3267; A61M 2005/206
 See application file for complete search history.

(56) References Cited

OTHER PUBLICATIONS

International Search Report and Written Opinion dated Nov. 11, 2016, for corresponding International Application No. PCT/GB2016/052569; International Filing Date: Aug. 19, 2016 consisting of 11-pages.
IPO Search Report dated Feb. 24, 2016, for Application No. GB1516219.1; Filing Date: Sep. 14, 2015 consisting of 3-pages.

* cited by examiner

INJECTION DEVICE

CROSS-REFERENCE TO RELATED APPLICATIONS

This application is a Submission under 35 U.S.C. § 371 for U.S. National Stage Patent Application of, and claims priority to, International Application Number PCT/GB2016/052569 entitled INJECTION DEVICE, filed Aug. 19, 2016, which is related to and claims priority to Great Britain Patent Number 1516219.1, filed Sep. 14, 2015, the entirety of all of which are incorporated herein by reference.

TECHNICAL FIELD

The invention relates to an injection device, particularly to an injection device having a needle shield.

BACKGROUND

Injection devices comprising automatically actuatable syringes, sometimes referred to as auto-injectors, are known. These devices include an energy source, for example a compressed spring or a container of pressurised gas, which is used to deliver a dose of medicament to a patient. Such devices may include further components, such as a needle protecting shield for selectively covering a needle of the device. The needle shield makes safe the device by covering the needle at certain stages of operation and reduces the risk of potential needle stick injuries. In a final needle protecting position, the needle shield may also prevent unintentional and/or undesirable re-use of the device.

It is an object of certain embodiments of the invention to provide an improved injection device. It is an object of embodiments of the invention to at least mitigate one or more of the problems associated with prior art arrangements.

SUMMARY OF THE INVENTION

According to the invention, there is provided an injection device comprising an outer housing configured to receive a syringe, the syringe having a barrel for containing medicament and a needle in fluid communication with the barrel;
  a needle shield axially moveable relative to the outer housing between a needle covering position and a needle exposing position to selectively provide a needle enclosure, the needle exposing position being axially rearward of the needle covering position;
  a biasing means for biasing the needle shield axially forwardly toward the needle covering position;
  a locking means; and
  a locking sleeve axially movable relative to the outer housing between a non-locking position and a locking position, the locking position being axially rearward of the non-locking position, in which axial movement of the locking sleeve is selectively limited by the locking means;
  wherein in a first configuration the needle shield is in the needle covering position and the locking sleeve is in the non-locking position so that at least a portion of the needle shield is axially slideable within the locking sleeve to permit rearward axial movement of the needle shield from the needle covering position to the needle exposing position; and
  in a subsequent configuration the needle shield is in the needle covering position and the locking sleeve is in the locking position so that the needle shield is prevented from moving axially rearwardly by interference with the locking sleeve. This arrangement may minimise the risk of potential needle stick injuries Preferably, rearward axial movement of the needle shield from the needle covering position to the needle exposing position causes axial movement of the locking sleeve from the non-locking position to the locking position.

In certain embodiments, the device further comprises a syringe carrier for supporting the syringe within the outer housing. Further, the syringe carrier may be axially moveable relative to the outer housing. The syringe carrier may be formed as a sleeve-like member at least partially surrounding a length of the barrel of the syringe.

Optionally, the device further comprises a syringe plug which cooperates with the syringe carrier to retain the syringe within the syringe carrier such that the syringe cannot move axially relative to the syringe carrier and the syringe plug. In certain embodiments, the syringe plug has an axially extending spigot for insertion into the barrel of the syringe to form a sealing fit between the spigot and the inside of the barrel.

The syringe plug may have a channel passing therethrough in fluid communication with the inside of the barrel of the syringe.

In certain embodiments, the locking means comprises at least one radial protrusion having a corresponding opening in which the radial protrusion is selectively received in order to lock the locking sleeve in the locking position. The at least one radial protrusion may formed as part of the locking sleeve and the corresponding opening may be formed as part of the outer housing, or vice versa, thereby preventing forward axial movement of the locking sleeve relative to the outer housing when the locking sleeve is in the locking position. Alternatively, the at least one radial protrusion may be formed as part of the locking sleeve and the corresponding opening may be formed as part of the syringe carrier, or vice versa, thereby preventing forward axial movement of the locking sleeve relative to the syringe carrier when the locking sleeve is in the locking position.

In certain embodiments, the at least one radial protrusion is formed as part of the locking sleeve and the corresponding opening is formed as part of the syringe plug, or vice versa, thereby preventing forward axial movement of the locking sleeve relative to the syringe plug when the locking sleeve is in the locking position.

The at least one radial protrusion may be provided at a free end of a flexible finger to permit radial displacement of the at least one radial protrusion.

Optionally, the needle shield comprises at least one radial protrusion selectively engageable with the locking sleeve to prevent the needle shield from moving axially rearwardly relative to the locking sleeve when the locking sleeve is in the locking position. The at least one radial protrusion of the locking sleeve may be a radially inward protrusion.

In certain embodiments, the needle shield further comprises at least one radially flexible arm having a free end upon which the at least one radial protrusion of the needle shield is provided. The needle shield may further comprise a main body from which the at least one radially flexible arm of the needle shield extends axially rearward, the main body of the needle shield forming at least in part the needle enclosure. The main body may have a wall to which the at least one radially flexible arm is parallel.

The at least one flexible arm of the needle shield may form a portion of the needle shield received within the locking sleeve.

In the first configuration, the at least one radial protrusion of the needle shield may be axially rearward of a forward facing abutment surface of the locking sleeve.

In the subsequent configuration, the at least one radial protrusion of the needle shield may be axially forward of, and at least partially axially aligned with, the forward facing abutment surface of the locking sleeve such that the at least one radial protrusion of the needle shield cannot move axially rearwardly of forward facing abutment surface of the locking sleeve.

In certain embodiments, the at least one radial protrusion of the needle shield is radially movable between a first radial position and a second radial position in order to selectively move into/out of axial alignment with the forward facing abutment surface of the locking sleeve, thereby permitting the at least one radial protrusion of the needle shield to move axially forward of the forward facing abutment surface of the locking sleeve. The second radial position of the at least one radial protrusion of the needle shield may be radially inward of the first radial position of the at least one radial protrusion of the needle shield.

Optionally, the locking sleeve comprises at least one radial protrusion selectively engageable with the needle shield to inhibit the needle shield from moving axially rearwardly relative to the locking sleeve when the locking sleeve is in the locking position. The at least one radial protrusion of the locking sleeve may be a radially inward protrusion. The locking sleeve may further comprise at least one radially flexible arm having a free end upon which the at least one radial protrusion of the locking sleeve is provided. The locking sleeve may further comprise a main body from which the at least one radially flexible arm of the locking sleeve extends axially forward.

In certain embodiments, the portion of the needle shield received within the locking sleeve is received within a portion of the locking sleeve formed by the at least one radially flexible arm of the locking sleeve. The locking sleeve is contained entirely within the outer housing.

In the first configuration, the at least one radial protrusion of the locking sleeve may be axially forward of a rearward facing abutment surface of the needle shield.

In certain embodiments, the at least one radial protrusion of the locking sleeve is axially rearward of, and at least partially axially aligned with, the rearward facing abutment surface of the needle shield such that the at least one radial protrusion of the locking sleeve cannot move axially forward of rearward facing abutment surface of the needle shield.

In certain embodiments, the at least one radial protrusion of the locking sleeve is radially movable between a first radial position and a second radial position in order to selectively move into/out of axial alignment with the rearward facing abutment surface of the needle shield, thereby permitting the at least one radial protrusion of the locking sleeve to move axially rearward of the rearward facing abutment surface of the needle shield.

The second radial position of the at least one radial protrusion of the needle shield may be radially inward of the first radial position of the at least one radial protrusion of the locking sleeve.

The forward facing abutment surface of the locking sleeve may formed on the at least one radial protrusion of the locking sleeve. The rearward facing abutment surface of the needle shield may be formed on the at least one radial protrusion of the needle shield.

In certain embodiments, the device further comprises an energy source actuatable to move the stopper axially forward within the barrel of the syringe. The energy source may comprise a fluid reservoir of a liquefied gas propellant. The outer housing may be configured to receive the energy source. The energy source may comprise a propellant which includes a hydrofluoroalkane ("HFA") and/or a hydrofluoroolefin ("HFO").

BRIEF DESCRIPTION OF THE DRAWINGS

The invention will now be described further, by way of example only, with reference to the accompanying figures, in which.

DETAILED DESCRIPTION

Figure 1:
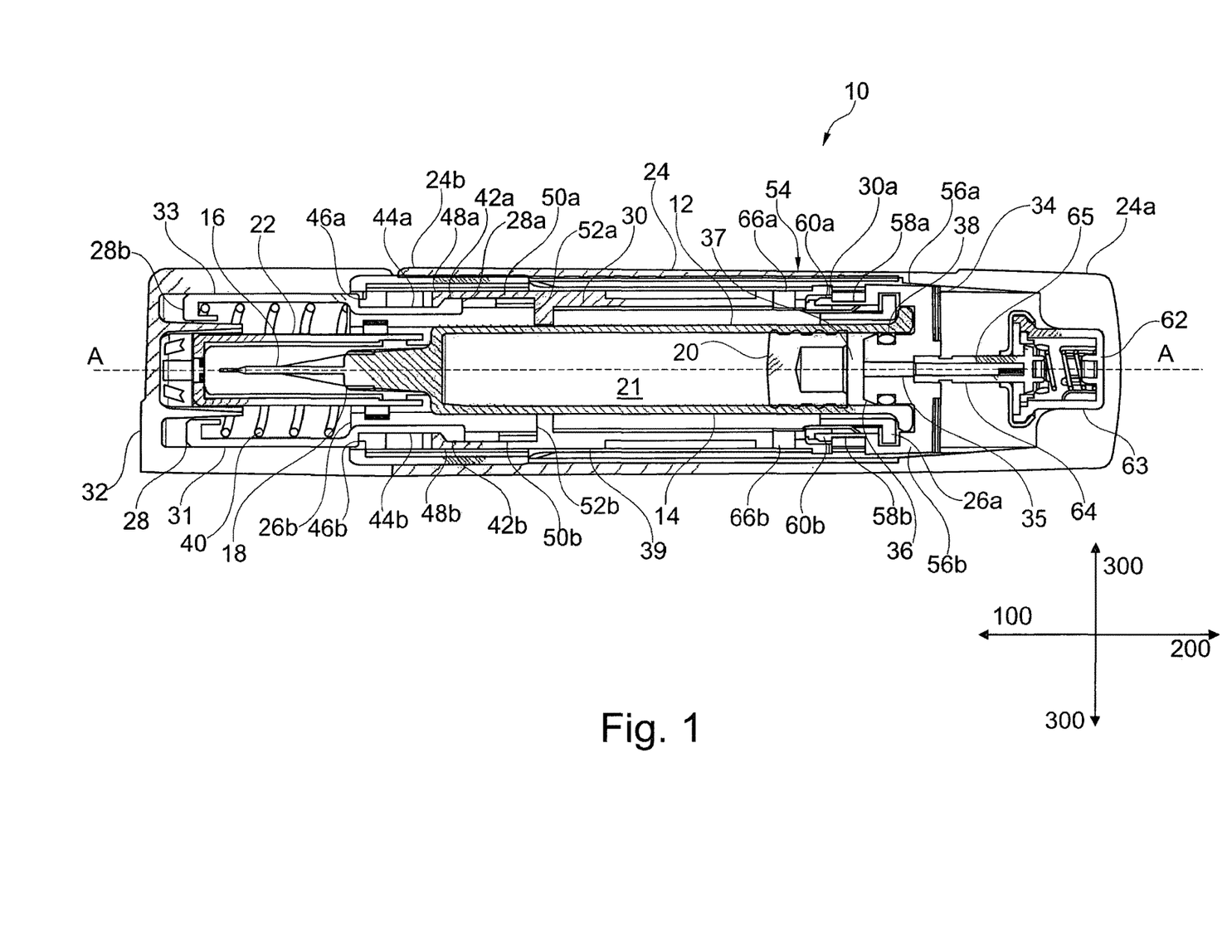
FIG. 1 is a cross-sectional side view of an injection device according to an embodiment of the invention.

FIGS. 1 to 6 illustrate an injection device 10 according to an embodiment of the invention. The device 10 is an auto-injector device 10 for delivering a dose of medicament to a patient. The device 10 includes a syringe 12 having a barrel 14 and a needle 16. The barrel 14 has an open end 18 to which the needle 16 is attached. The barrel 14 also contains a stopper 20 axially slideable therein. The barrel 14 and the stopper 20 together define a first volume 21 axially forward of the stopper 20 for containing medicament. Note that references to the forward axial direction are intended to mean towards the open end 18 of the barrel 14, i.e. parallel to direction 100 shown in FIG. 1. Conversely, references to the rearward axial direction are intended to mean away from the open end 18 of the barrel 14, i.e. parallel to the direction 200 shown in FIG. 1. References to radial directions are intended to mean any direction perpendicular to the forward and rearward axial directions 100, 200 with respect to a longitudinal axis A of the device 10, as shown in FIG. 1. Directions 300 are parallel to the radial directions in the cross-sectional plane of the device 10 shown in FIG. 1.

Medicament contained within the first volume 21 may be expelled via the open end 18 in response to forward axial movement of the stopper 20 within the barrel 14. The syringe 12 may also include a removable needle sheath 22 for covering the needle prior to use. The device 10 further includes an outer housing 24 configured for receiving the syringe 12 such that the syringe 12 is axially moveable within the housing 24. In the illustrated embodiment, the syringe 12 is supported within the outer housing 24 by a syringe carrier 26. A protective needle shield 28 is provided at the front end of the device 10 to selectively cover the needle 16 of the syringe 12. The device 10 also includes a locking sleeve 30 configured to at least partially receive the syringe carrier 26, as is described in further detail below.

In the illustrated embodiment, the outer housing 24 is a substantially tubular element configured to contain multiple components of the device 10. The outer housing 24 has a closed end 24a and an open end 24b. The closed end 24a is at the rear of the device 10 and the open end 24b is at the front of the device 10. The open end 24b is configured to engage with a safety cap 32 which, when engaged, surrounds the needle 16 and the needle sheath 22. The housing 24 and safety cap 32 may be engageable by means of a push-fit connection, a snap-fit connection, a bayonet connection or by cooperating threaded portions provided on the open end 24b of the housing 24 and the cap 32, respectively. The housing 24 and safety cap 32 may be engageable by any suitable means. The device 10 cannot be used to deliver a dose of medicament when the safety cap 32 is connected to the open end 24b of the housing 24. In certain embodiments, the cap 32 may incorporate means to remove the removable needle sheath 22 upon removal of the cap 32 from the outer housing 24. In certain embodiments, the external profile of the outer housing 24 may be of an ergonomic design to accommodate the grip of a user, thus facilitating easy use of the device 10.

The syringe carrier 26 is a substantially sleeve-like member which at least partially surrounds the length of the barrel 14 of the syringe 12. Further, the syringe carrier 26 is configured to be axially movable within the outer housing 24. In certain embodiments, axial movement of the syringe carrier 26 within the housing 24 may result in axial movement of the syringe 12 relative to the housing 24. Moreover, the syringe carrier 26 and the syringe 12 may move axially within the housing 24 together as one. In the illustrated embodiment, the syringe carrier 26 cooperates with a syringe plug 34 to retain the syringe 12 within the syringe carrier 26. The syringe plug 34 includes an axially extending spigot 36 for insertion into the rear of the barrel 14. As shown in the accompanying figures, the spigot 36 may include a seal 38 for facilitating a sealing fit between the spigot 36 and the inside of the barrel 14. The seal 38 may be an O-ring seal 38. The barrel 14, the stopper 20 and the plug 34 together partially define a second volume 37 axially rearward of the stopper 20. The plug 34 has a channel 35 passing therethrough such that the channel 35 is fluidly connected with the second volume 37. The syringe plug 34 further includes latch members 56a, 56b. In the illustrated embodiment, the latch members 56a, 56b are diametrically opposed about the spigot 36 and configured to engage with a rear end 26a of the syringe carrier 26 so as to retain the spigot 36 within the barrel 14 of the syringe 12 and the syringe 12 within the syringe carrier 26. In certain embodiments, only one of the latch members 56a, 56b may be provided. Alternatively, more than two of the latch members 56a, 56b may be provided and/or the latch members 56a, 56b may not be diametrically opposed about the spigot 36. In certain embodiments, the latch members may engage with the syringe 12.

The needle shield 28 is a substantially tubular member configured to selectively provide a protective enclosure around the needle 16. The needle shield 28 has an aperture 29 at a front end 28b of the needle shield 28 configured to permit passage therethrough of at least the needle 16. In certain embodiments, the aperture 29 may be configured to permit passage of the syringe 12. A rear end 28a of the needle shield 28 is a substantially open end to allow engagement with other components of the device 10. The needle shield 28 may partially extend through the open end 24b of the outer housing 24 such that at least a portion of the needle shield 28 is received within the housing 24. As shown in the illustrated embodiment, the needle shield 28 may be mounted to a front end 26b of the syringe carrier 26. Moreover, the front end 26b of the syringe carrier 26 may be received within the needle shield 28 such that the needle shield 28 is axially movable relative to the syringe carrier 26 in a telescopic manner.

The needle shield 28 is configured to be axially moveable relative to the outer housing 24 between a needle covering position and a needle exposing position, the needle exposing position being axially rearward of the needle covering position. The needle shield 28 is biased axially forwardly toward the needle covering position by a biasing means 40. As shown in the illustrated embodiment, the biasing means 40 may comprise a helical compression spring 40. The spring 40 may be retained between an inner surface of the front end 28b of the needle shield 28 and the front end 26b of the syringe carrier 26. The spring 40 is provided within the needle shield 28 such that at least the open end 18 of the syringe 12 and/or the needle 16 may extend in an axial direction through the centre of the spring 40 and therefore extend in an axial direction through the needle shield 28.

The locking sleeve 30 is a substantially sleeve-like member configured to be axially moveable within the housing 24. As mentioned above, the locking sleeve 30 is configured to at least partially receive the syringe carrier 26. Specifically, in the illustrated embodiment, the locking sleeve 30 and the syringe carrier 26 are concentric tubular sections in which the syringe carrier 26 is axially moveable within the locking sleeve 30. In certain embodiments, the locking sleeve 30 may be entirely contained within the outer housing 24. Such arrangement may prevent the user from impeding the axial movement of the locking sleeve 30. The locking sleeve 30 is axially moveable relative to the outer housing 24 between a non-locking position and a locking position, the locking position being axially rearward of the non-locking position. The locking sleeve 30 is able to move axially rearward relative to the housing 24 when in the non-locking position. However, once in the locking position, axial movement of the locking sleeve 30 is limited. Particularly, forward axial movement of the locking sleeve 30 relative to the outer housing 24 may be prevented when the locking sleeve 30 is in the locking position. In the non-locking position, at least a portion of the needle shield 28 is received within the locking sleeve 30 and is axially slideable therein.

The needle shield 28 includes a plurality of radially outward protrusions 42a, 42b. The radial protrusions 42a, 42b of the needle shield 28 may provide a first rearward facing abutment surface of the needle shield 28. As shown in the illustrated embodiment, each of the plurality of protrusions 42a, 42b of the needle shield 28 may be formed on respective free ends of a plurality of flexible arms 44a, 44b of the needle shield 28. In certain embodiments, the flexible arms 44a, 44b of the needle shield 28 may be provided such that they extend axially rearwardly of a main body 31 of the needle shield 28 from their fixed ends. The main body 31 has a wall 33, to which the arms 44a, 44b may extend substantially parallel. The main body 31 of the needle shield 28 may form at least a part of the protective enclosure which is selectively provided around the needle 16. The flexible arms 44a, 44b of the needle shield 28 may form at least part of the portion of the needle shield 28 received within the locking sleeve 30. To this end, each of the flexible arms 44a, 44b of the needle shield 28 may include a respective step 46a, 46b adjacent their fixed ends, such that the arms 44a, 44b extend parallel to and radially inward relative to the wall 33 of the main body 31. This arrangement may facilitate the insertion of the needle shield 28 into the locking sleeve 30. The steps 46a, 46b may provide a second rearward facing abutment surface of the needle shield 28.

The flexible arms 44a, 44b of the needle shield 28 may flex, i.e. elastically deform, radially inwardly in response to a radially inward force applied thereto. The flexible arms 44a, 44b of the needle shield 28, when flexed, are biased toward a non-flexed condition by virtue of their flexural rigidity, i.e. when the force causing flexing is removed they will naturally spring back from a flexed condition toward a non-flexed condition. Therefore, in the absence of an applied radially inward force, the flexible arms 44a, 44b will be in a non-flexed condition.

The locking sleeve 30 includes a plurality of first radially inward protrusions 48a, 48b. The first radial protrusions 48a, 48b of the locking sleeve 30 provide a first forward facing abutment surface of the locking sleeve 30. As shown in the illustrated embodiment, each of the plurality of first inward protrusions 48a, 48b of the locking sleeve 30 may be formed on respective free ends of a plurality of flexible arms 50a, 50b of the locking sleeve 30. The flexible arms 50a, 50b of the locking sleeve 30 are provided such that they extend axially forwardly of a main body 39 of the locking sleeve 30 from their fixed ends. The portion of the needle shield 28 received within the locking sleeve 30 may be received by the flexible arms 50a, 50b of the locking sleeve 30 in a telescoping manner. The locking sleeve 30 is provided with a plurality of second radially inward protrusions 52a, 52b adjacent the fixed ends of the plurality of flexible arms 50a, 50b of the locking sleeve 30. The plurality of second radially inward protrusions 52a, 52b may provide a second forward facing abutment surface of the locking sleeve 30. In certain embodiments, the plurality of second radially inward protrusions 52a, 52b may instead be an annular flange projecting radially inwardly from an inside surface of the locking sleeve 30 adjacent the fixed ends of the plurality of flexible arms 50a, 50b of the locking sleeve 30.

The flexible arms 50a, 50b of the locking sleeve 30 may flex, i.e. elastically deform, radially outwardly in response to a radially outward force applied thereto. The flexible arms 50a, 50b of the locking sleeve 30, when flexed, are biased toward a non-flexed condition by virtue of their flexural rigidity, i.e. when the force causing flexing is removed they will naturally spring back from a flexed condition toward a non-flexed condition. Therefore, in the absence of an applied radially outward force, the flexible arms 50a, 50b will be in a non-flexed condition.

The device 10 also includes locking means 54 configured to lock the locking sleeve 30 in the locking position, i.e. to limit axial movement of the locking sleeve 30. In the illustrated embodiment, the locking means 54 is configured to prevent forward axial movement of the locking sleeve 30 relative to the syringe carrier 26. However, in certain embodiments, the locking means 54 may be configured to prevent forward axial movement of the locking sleeve 30 relative to the outer housing 24. In the illustrated embodiment, the locking means 54 includes flexible fingers 58a, 58b formed as part of the plug 34. Specifically, the flexible fingers 58a, 58b may extend axially forwardly of the latch members 56, 56b from their respective free ends. The flexible fingers 58a, 58b have retaining means at their free ends which are configured to selectively engage with a rear end 30b of the locking sleeve 30. The retaining means may comprise radially outward protrusions 60a, 60b of the flexible fingers 58a, 58b. The flexible fingers 58a, 58b may flex, i.e. elastically deform, radially inward in response to a radially inward force applied thereto. The flexible fingers 58a, 58b, when flexed, are biased toward a non-flexed condition by virtue of their flexural rigidity, i.e. when the force causing flexing is removed they will naturally spring back from a flexed condition toward a non-flexed condition. Therefore, in the absence of an applied radially inward force, the flexible fingers 58a, 58b will be in a non-flexed condition. In certain embodiments, the flexible fingers may be provided on the syringe carrier 26.

The device 10 further includes an energy source 62. In the illustrated embodiment, the energy source 62 comprises a propellant source 62 having a fluid reservoir 63 for containing a propellant. The propellant source 62 is accommodated in the closed end 24a of the outer housing 24 axially rearward of the syringe 12. However, in certain embodiments, the energy source 62 may not be axially rearward of the syringe 12. Moreover, there is no requirement for the energy source 62 to be axially aligned with the longitudinal axis A, as shown in the accompanying figures. As illustrated in the accompanying figures, the outer housing 24 may be formed to locate and/or support the propellant source 62. In the illustrated embodiment, the propellant source 62 includes an axially extending stem 64 having a bore 65 selectively fluidly connecting the fluid reservoir 63 of the propellant source 62 to the axial channel 35. Therefore, the fluid reservoir 63 of the propellant source 62 is selectively fluidly connected to the second volume 37, which is partially defined by the barrel 14, the stopper 20 and the plug 34. Of course, it will be understood that in other embodiments the exact arrangement may differ, particularly if the energy source 62 is other than the propellant source 62 described above. The stem 64 is slidably engaged with the fluid reservoir 63 such that axial compression of the propellant source 62 causes at least a portion of the stem 64 to move axially into the fluid reservoir 63. The axial compression of the propellant source 62 opens a valve and/or unseats a seal within the reservoir 63 so that bore 65 of the stem 64 is fluidly connected to the reservoir 63. The propellant source 62 is in an open condition when the bore 65 of the stem 64 is fluidly connected to the reservoir 63. The propellant source 62 is in a closed condition when the bore 65 of the stem 64 is not fluidly connected to the reservoir 63. The propellant may be any suitable propellant for providing a vapour pressure to the second volume 37. In certain embodiments, the propellant may be a liquefied gas that vaporises to provide a vapour pressure. In certain embodiments, the propellant may be or contain a hydrofluoroalkane ("HFA"), for example HFA 134a, HFA227, HFA 422D, HFA 507, or HFA 410A. Alternatively or additionally, the propellant may be or contain a hydrofluoroolefin ("HFO") such as HFO 1234yf or HFO 1234ze.

FIGS. 1 to 6 illustrate the device 10 at various stages of operation, including delivery of the medicament to a patient. During delivery, the medicament is expelled from the device 10 into an injection site, e.g. soft tissue of the patient. The various stages of operation may be defined by the respective axial positions of at least the needle shield 28 and the locking sleeve 30.

FIG. 1 illustrates the device 10 in a pre-use condition, in which the syringe 12 is pre-filled with a dose medicament for delivery to the patient. In particular, the safety cap 32 is connected to the open end 24b of the outer housing 24 such that the needle 16 is not visible to the user and/or the patient. Further, the propellant source 62 is in a closed configuration such that no propellant may exit the propellant source 62 and enter the second volume 37. FIG. 1 illustrates the needle shield 28 and the locking sleeve 30 in a first configuration. In the first configuration, the needle shield 28 is in the needle covering position and the locking sleeve 30 is in the non-locking position. At least a portion of the needle shield 28 is axially slidable within the locking sleeve 30 to permit rearward axial movement of the needle shield 28 from the needle covering position to the needle exposing position. Of course, with safety cap 32 connected to the open end 24b of the outer housing 24 it is not possible for the needle shield 28 to be moved axially in relation to the housing 24 by action of the user. The device 10 is needle safe when in the pre-use condition, i.e. it is not possible to expose the needle 16.

As shown in the illustrated embodiment, when the device 10 is in the first configuration the radially outward protrusions 42a, 42b of the needle shield 28 are axially rearward of the first radially inward protrusions 48a, 48b of the locking sleeve 30. Further, the radially outward protrusions 42a, 42b of the needle shield 28 and the plurality of first radially inward protrusions 48a, 48b of the locking sleeve 30 are at least partially axially aligned. Therefore, notwithstanding any interaction with other components of the device 10, for the radially outward protrusions 42a, 42b of the needle shield 28 to move axially forward of the first radially inward protrusions 48a, 48b of the locking sleeve 30, the radially outward protrusions 42a, 42b of the needle shield 28 and/or the first radially inward protrusions 48a, 48b of the locking sleeve 30 must be radially displaced such that they are no longer axially aligned. Prior to use of the device 10, the flexible arms 44a, 44b of the needle shield 28 may be in a substantially non-flexed condition. However, in certain embodiments, the flexible arms 44a, 44b of the needle shield 28 may be held in a flexed condition radially inwardly of their non-flexed condition prior to use of the device 10. Further, in certain embodiments, the flexible arms 48a, 48b of the locking sleeve 28 may be held in a flexed condition radially outward of their non-flexed condition prior to use of the device 10. Either of these arrangements may arise when the needle shield 28 is inserted into the locking sleeve 30. Holding the flexible arms 44a, 44b, 50a, 50b of at least one of the needle shield 28 or the locking sleeve 30 in a flexed condition may ensure that the respective protrusions 42a, 42b, 48a, 48b are radially aligned with one another when the needle shield 28 is inserted into the locking sleeve 30.

Figure 2:
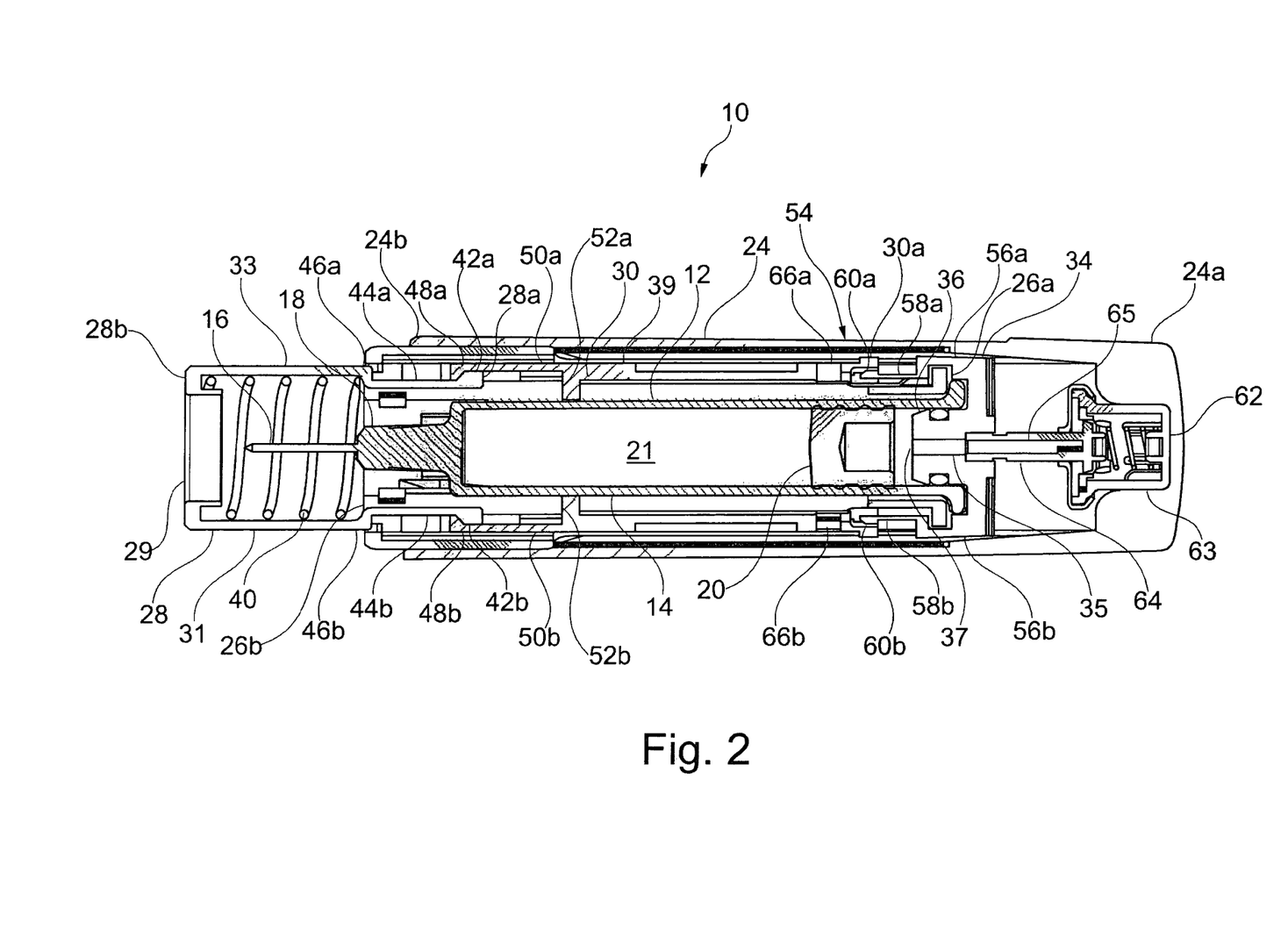
FIG. 2 is a cross-sectional side view of the device shown in FIG. 1 ready to be used to deliver a dose of medicament.

FIG. 2 shows the device 10 in a condition in which it is ready for use. To ready the device 10 for use the safety cap 32 must be removed from the open end 24b of the outer housing 24, thus partially exposing the needle shield 28 at the front of the device 10. Following the removal of the cap 32 the needle shield 28 and the locking sleeve 30 remain in the first configuration. While the needle shield 28 partially hides the needle 16 from view, the needle 16 may now be visible if viewed through the aperture 29 in the front end 28b of the needle shield 28. However, it remains difficult for the needle 16 to be seen by the patient and this may help to reduce patient anxiety associated with needle phobia. To administer the dose of medicament, the device 10 is positioned with the front end 28b of the needle shield 28 at the injection site and a forward axial force is exerted upon the outer housing 24 to press the device 10 against the injection site. The housing 24 moves axially forwardly towards the injection site in response to the force, thus causing the needle shield 28 to move axially rearwardly relative to the housing 24, i.e. the needle shield 28 moves into the housing 24 as the needle shield 28 does not move relative to the injection site. As the needle shield 28 moves axially rearwardly relative to the housing 24, the spring 40 is compressed.

Figure 3:
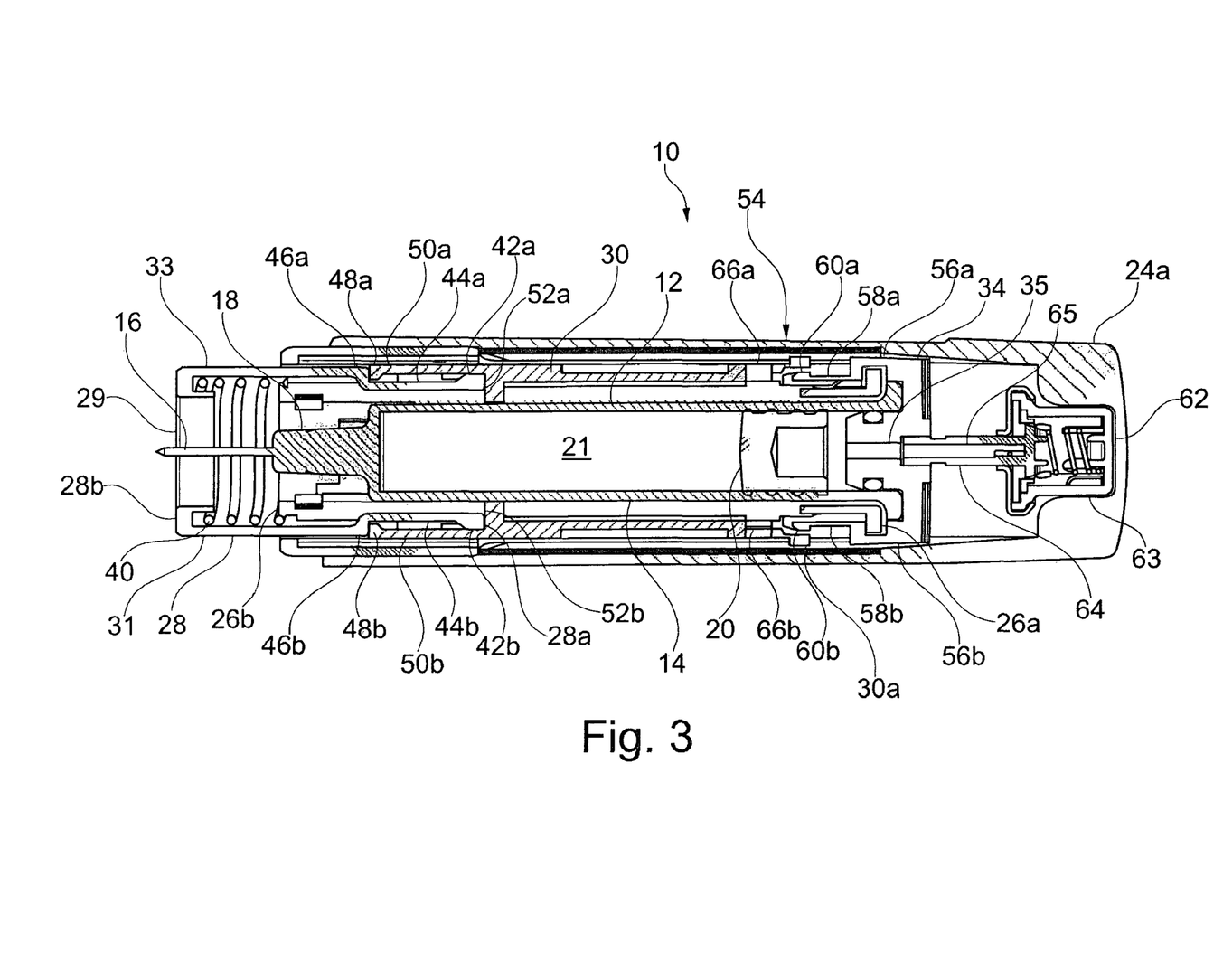
FIG. 3 is a cross-sectional side view of the device shown in FIGS. 1 and 2 as it would appear partially pressed against an injection site prior to delivery of the medicament.

FIG. 3 illustrates the device 10 as it would appear when only partially pressed against the injection site. FIG. 3 illustrates the needle shield 28 and the locking sleeve 30 in a second configuration. In the second configuration, the needle shield 28 has moved axially rearwardly relative to the housing 24 when compared to the first configuration (shown in FIGS. 1 and 2). In the second configuration, the needle shield 28 can no longer move axially rearwardly relative to the locking sleeve 30. In particular, further rearward axial movement of the needle shield 28 relative to the locking sleeve 30 is prevented by interference of the needle shield 28 and the locking sleeve 30. Specifically, the rearward facing abutment surfaces of the needle shield 28 contact the forward facing abutment surfaces of the locking sleeve 30. In the illustrated embodiment, this arises as the radially outward protrusions 42a, 42b of the needle shield 28 contact the plurality of second radially inward protrusions 52a, 52b of the locking sleeve 30. Additionally, inward steps 46a, 46b of the needle shield 28 contact the plurality of first radially inward protrusions 48a, 48b of the locking sleeve 30. In the second configuration, the propellant source 62 remains in a closed condition such that no propellant may exit the propellant source 62. Further, in the second configuration, the needle 16 may be at least partially exposed axially forward of the needle shield 28. Therefore, the needle 16 may begin to penetrate the injection site since the needle 16 has moved axially forward relative to the needle shield 28 to extend beyond the front end 28b of the needle shield 28. In certain embodiments, a clearance may be maintained between the rearward facing abutment surfaces of the needle shield 28 and the forward facing abutment surfaces of the locking sleeve 30. Rearward axial movement of the needle shield 28 relative to the locking sleeve 30 may be inhibited by contact between the needle shield 28 and the locking sleeve 30 other than by contact of the rearward facing abutment surfaces of the needle shield 28 and the forward facing abutment surfaces of the locking sleeve 30

Figure 4:
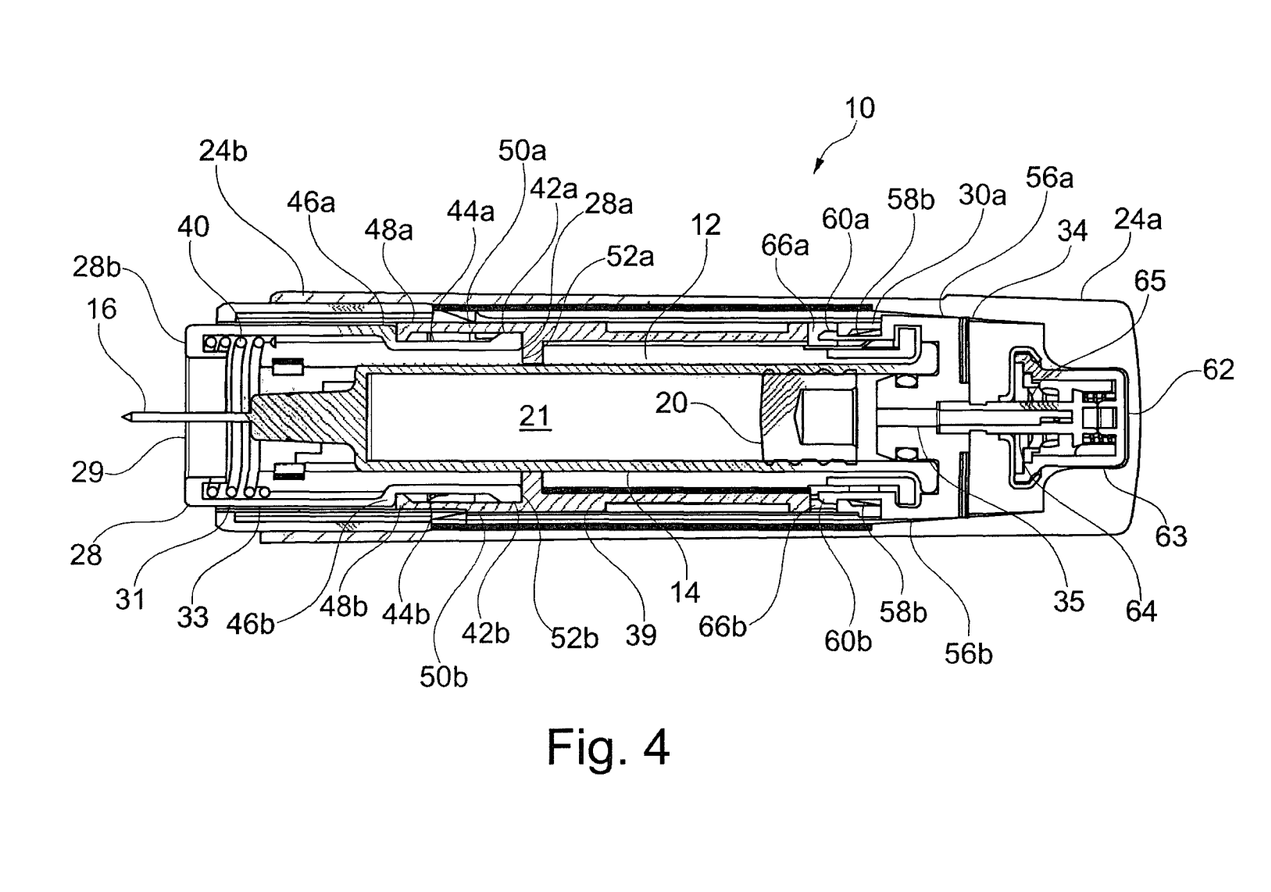
FIG. 4 is a cross-sectional side view of the device shown in FIGS. 1 to 3 as it would appear fully pressed against an injection site during delivery of the medicament.

In the second configuration, continued rearward axial movement of the needle shield 28 relative to the outer housing 24 remains possible. However, such continued rearward axial movement of the needle shield 28 requires rearward axial movement of the locking sleeve 30 within the outer housing 24 relative to the syringe carrier 26. In the illustrated embodiment, continued rearward axial movement of the needle shield 28 relative to the outer housing 24 pushes the locking sleeve 30 axially rearward within the outer housing 24 until the rear end 30a of the locking sleeve 30 contacts the syringe plug 34. However, as in the illustrated embodiment, the flexible fingers 58a 58b of the syringe plug 34 may be in the axial path of the locking sleeve 30. Consequently, upon contact between the rear end 30a of the locking sleeve 30 and the radially outward protrusions 60a, 60b of the flexible fingers 58a, 58b, further continued rearward movement of the locking sleeve 30 causes the protrusions 60a, 60b to be displaced radially out of the axial path of the locking sleeve 30. The radial displacement of the protrusions 60a, 60b may be by cam action, i.e. a chamfered surface provided on the radially outward protrusions 60a, 60b of the flexible fingers 58a, 58b, the locking sleeve 30, or both causes a radially inward force to be applied to flexible fingers 58a, 58b as locking sleeve 30 and the protrusions 60a, 60b contact one another. In the illustrated embodiment, the flexible fingers 58a, 58b flex radially inward in response to this radially inward force thereby permitting the rear end 30a of the locking sleeve 30 to move axially rearward of radially outward protrusions 60a, 60b of the flexible fingers 58a, 58b. Subsequently, the locking sleeve 30 contacts the latch members 56a, 56b of the syringe plug 34. Continued rearward axial movement of the locking sleeve 30 may push the syringe plug 34 axially rearward, thereby axially compressing the propellant source 62, as shown in FIG. 4. Alternatively, the locking sleeve 30 may cooperate with the syringe 12, the syringe carrier 26, or the propellant source 62 itself to compress propellant source 62.

FIG. 4 depicts the device 10 with the needle shield 28 and the locking sleeve 30 pushed completely axially rearwardly within the housing 24, such that further rearward axial movement of the needle shield 28 and the locking sleeve 30 relative to the housing 24 is not possible. FIG. 4 illustrates the needle shield 28 and the locking sleeve 30 in a third configuration. In the third configuration, the needle shield 28 is in the needle exposing position and the locking sleeve 30 is in the locking position, the locking position being axially rearward of the non-locking position. In the third configuration, the needle 16 penetrates the injection site to a desire depth. Rearward axial movement of the needle shield 28 from the needle covering position to the needle exposing position causes axial movement of the locking sleeve 30 from the non-locking position to the locking position. In the illustrated embodiment, the radially outward protrusions 60a, 60b of the flexible fingers 58a, 58b are disposed in openings 66a, 66b on the locking sleeve 30 by virtue of the flexural rigidity of the flexible fingers 58a, 58b, thereby causing the flexible fingers 58a, 58b to elastically relax from a radially outward flexed position. This arrangement locks the locking sleeve 30 in the locking position. In the third configuration, the propellant source 62 is in an open configuration as described above. As propellant is introduced into the second volume 37 the vapour pressure therein will increase. The vapour pressure will increase until it is sufficient to provide a forward axial force on the stopper 20 capable of overcoming the static frictional forces between the stopper 20 and the barrel 14 in addition to the fluid resistance provided by the medicament contained within the first volume 21. Consequently, when a sufficient vapour pressure is reached, the stopper 20 will begin to move axially forwardly in the barrel 14, thereby causing the medicament to be expelled from the syringe 12 via the open end 18 of the syringe 12.

Figure 5:
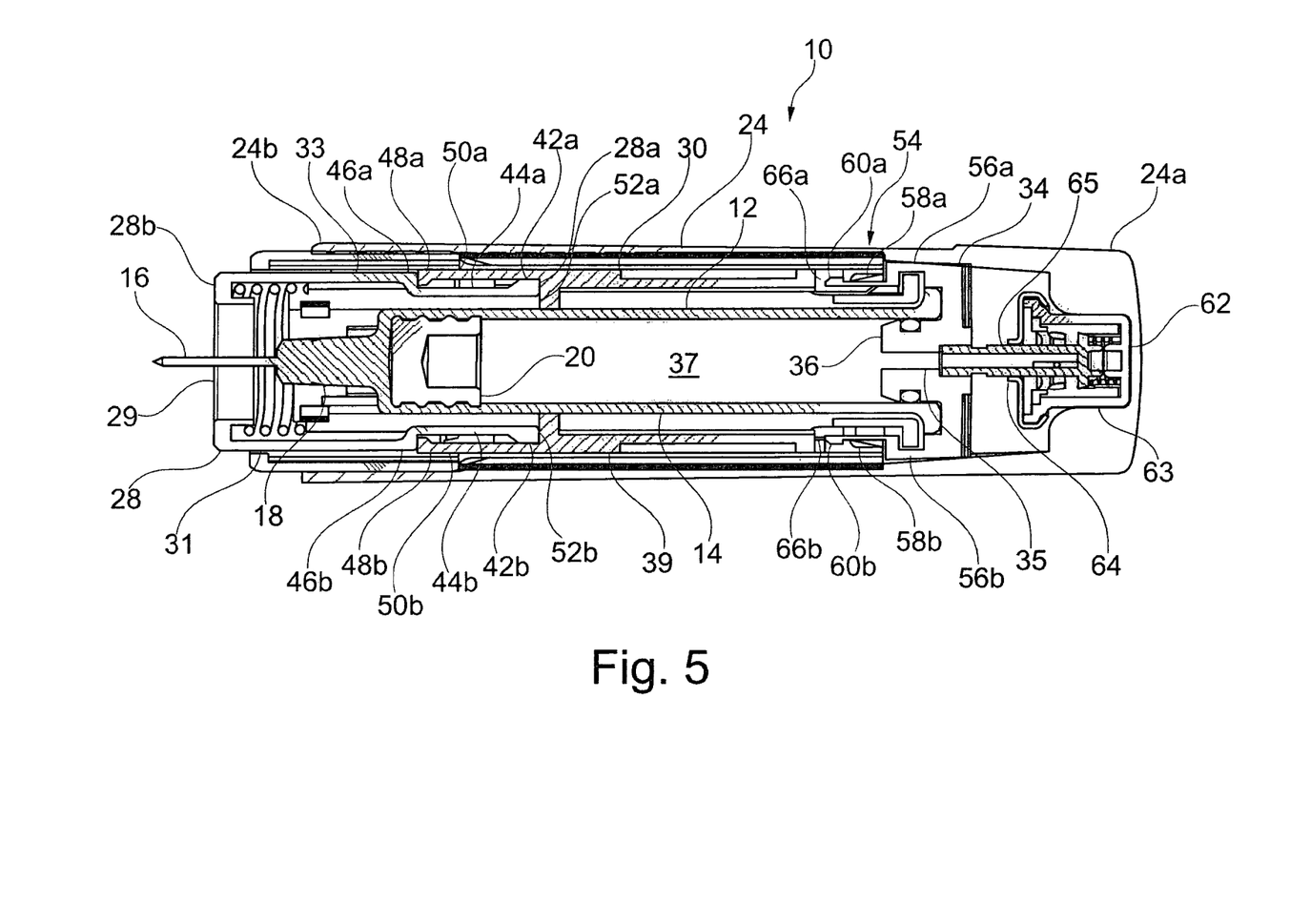
FIG. 5 is a cross-sectional side view of the device shown in FIGS. 1 to 4 as it would appear fully pressed against an injection site after delivery of the medicament.

FIG. 5 shows the device 10 as it would appear following completed delivery of the medicament while still fully pressed against the injection site, i.e. with the needle 16 still penetrating the injection site. FIG. 5 illustrates the needle shield 28 and the locking sleeve 30 in a fourth configuration, in which the needle shield 28 remains in the needle exposing position and the locking sleeve 30 remains in the locking position. The stopper 20 has moved axially forwardly within the barrel 14 of the syringe 12 relative the axial position of the stopper 20 shown in FIG. 4. The user removes the device 10 from the injection site by application of an axially rearward force on the outer housing 20. This action withdraws the needle 16 from the injection site. Moreover, as the device 10 is removed from the injection site, the needle shield 28 is no longer prevented from moving axially forwardly relative to the housing 24. Consequently, the spring 40 biases the needle shield 28 axially forwardly relative to the housing 24 to cover the needle 16, i.e. the needle shield 28 moves out of the housing 24.

As the needle shield 28 moves axially forwardly relative to the housing 24, the plurality radially outward protrusions 42a, 42b of the needle shield 28 contact the first radially inward protrusions 48a, 48b of the locking sleeve 30. Continued forward axial movement of the needle shield 28, in response to biasing means 40 biasing the needle shield 28 axially forwardly relative to the housing 24, causes the radially outward protrusions 42a, 42b of the needle shield 28 and the first radially inward protrusions 48a, 48b of the locking sleeve 30 to be displaced radially. The displacement of the protrusions 42a, 42b, 48a, 48b may be by cam action. Chamfered surfaces provided on the protrusions 42a, 42b, 48a, 48b may cause a radially inward force to be applied to the flexible arms 44a, 44b of the needle shield 28 and a radially outward force to be applied to the flexible arms 50a, 50b of the locking sleeve 30 as the radially outward protrusions 42a, 42b of the needle shield 28 and the first radially inward protrusions 48a, 48b of the locking sleeve 30 contact one another.

In the illustrated embodiment, the flexible arms 44a, 44b of the needle shield 28 flex radially inward in response to the abovementioned radially inward force. Therefore, the radially flexible arms 44a, 44b of the needle shield 28 flex such that the radially outward protrusions 42a, 42b of the needle shield 28 move between a first radial position and a second radial position, the second radial position being radially inward of the first radial position. Further, in the illustrated embodiment, the flexible arms 50a, 50b of the locking sleeve 30 flex radially outward in response to the abovementioned radially outward force. Therefore, the radially flexible arms 50a, 50b of the locking sleeve 30 flex such that the first radially inward protrusions 48a, 48b of the locking sleeve 30 move between a first radial position and a second radial position, the second radial position being radially outward of the first radial position. Consequently, the radially outward protrusions 42a, 42b of the needle shield 28 may move axially forward of the first radially inward protrusions 48a, 48b of the locking sleeve 30, as they are no longer axially aligned with one another. Of course, the spring force of spring 40 must be high enough to overcome the force required to flex the flexible arms 44a, 44b, 50a, 50b of at least the needle shield 28 or the locking sleeve 30. The first radially inward protrusions 48a, 48b of the locking sleeve 30 are not moved axially forwardly upon contact with the radially outward protrusions 42a, 42b of the needle shield 28 as the locking sleeve 30 is in the locking position. Once the radially outward protrusions 42a, 42b of the needle shield 28 are axially forward of the first radially inward protrusions 48a, 48b of the locking sleeve 30, the flexible arms 44a, 44b, 50a, 50b return to their respective non-flexed conditions and thus the radially outward protrusions 42a, 42b of the needle shield 28 and the plurality of first radially inward protrusions 48a, 48b of the locking sleeve 30 are again at least partially axially aligned. In certain embodiments, only the flexible arms 44a, 44b, 50a, 50b of one of the needle shield 28 or the locking sleeve 30 may move radially to allow the radially outward protrusions 42a, 42b of the needle shield 28 to move axially forward of the first radially inward protrusions 48a, 48b of the locking sleeve 30.

Figure 6:
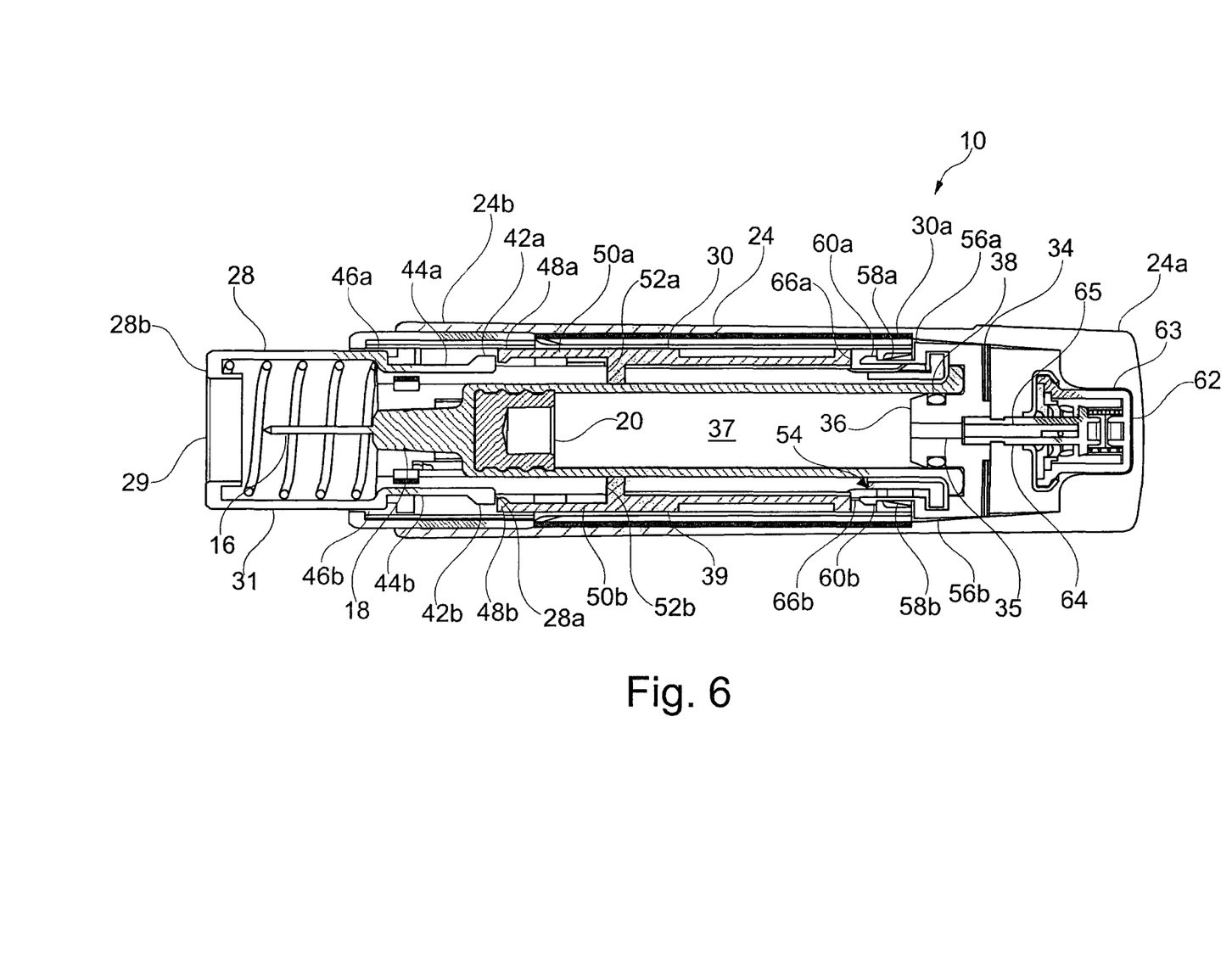
FIG. 6 is a cross-sectional side view of the device shown in FIGS. 1 to 5 after removal of the device from the injection site.

FIG. 6 illustrates the device 10 with the needle shield 28 fully extended following delivery of the dose of medicament and the subsequent removal of the device 10 from the injection site. FIG. 6 illustrates the needle shield 28 and the locking sleeve 30 in a fifth configuration, in which the needle shield 28 is in the needle covering position and the locking sleeve 30 is in the locking position so that the needle shield 28 is prevented from moving axially rearwardly by interference with the locking sleeve 30. Specifically, the first rearward facing abutment surface of the needle shield 28 contacts the first forward facing abutment surface of the locking sleeve 30. Rearward axial movement of the needle shield 28 is prevented by axial abutment between the radially outward protrusions 42a, 42b of the needle shield 28 and the plurality of first radially inward protrusions 48a, 48b of the locking sleeve 30. This arrangement means that the device 10 is "needle safe" in the fifth configuration, as the needle 16 cannot be exposed axially forward of the needle shield 28. The front end 28a of the needle shield 28 may be configured to prevent the locking sleeve 30 from being forced within the needle shield, to this end the front end 28a of the needle shield 28 may have a step (not shown). The clearance between an inside wall of the outer housing 24 and the flexible arms 48a, 48b of the locking sleeve 30 may prevent the flexible arms 48a, 48b from passing radially outward of the radial outward protrusions 42a, 42b of the needle shield 28. Additionally or alternatively, the syringe 12 or the syringe carrier 26 may prevent the radial outward protrusions 42a, 42b of the needle shield 28 from flexing radially inwards.

Certain embodiments of the invention intend to make safe the device 10 by covering the needle 16 at certain stages of operation, thereby minimising the risk of potential needle stick injuries. Also, when the needle shield 28 is locked in the needle covering position, the device 10 may also prevent unintentional or undesirable re-use of the needle 16 and syringe 12. Needle stick injuries and re-use of the needle 16 and syringe 12 may lead to accidental transmission of communicable diseases such as hepatitis or human immunodeficiency virus ("HIV"). Therefore, the above-described embodiment of the invention may help reduce inadvertent transmission of such diseases. As previously mentioned, covering the needle 16 during operation, thus hiding it from view of the patient, may also help to reduce patient anxiety associated with needle phobia, particularly when the device 10 is used to administer medicament to children and for self-administration.

The claimed arrangement, specifically in which at least a portion of the needle shield 28 is axially slideable within the locking sleeve 30 to permit rearward axial movement of the needle shield 28 within the device, allows the locking sleeve 30 to fit closely to the syringe 12. Such an arrangement offers potentially reduced diameter injection devices when compared to known arrangements.

The invention is not restricted to the details of any foregoing embodiments and many variations in design detail are possible within the scope of the appended claims. For example, in certain embodiments flexible arms may not be provided on both the needle shield and locking sleeve. A single flexible arm having a radial protrusion may be provided on either the needle shield or the locking sleeve, the radial protrusion being configured to engage with whichever of the needle shield or locking sleeve does not have the flexible finger. In certain embodiments, the locking means may be alternately provided. For example, the locking means may not be provided as part of the syringe plug. In certain embodiments, a latch member may be provided on the locking sleeve and configured to engage with the outer housing or the syringe carrier.

The invention extends to any novel one, or any novel combination, of the features disclosed in this specification (including any accompanying claims and drawings), or to any novel one, or any novel combination, of the steps of any method or process so disclosed. The claims should not be construed to cover merely the foregoing embodiments, but also any embodiments which fall within the scope of the appended claims.

All of the features disclosed in this specification (including any accompanying claims and drawings), and/or all of the steps of any method or process so disclosed, may be combined in any combination, except combinations where at least some of such features and/or steps are mutually exclusive.

Each feature disclosed in this specification (including any accompanying claims and drawings), may be replaced by alternative features serving the same, equivalent or similar purpose, unless expressly stated otherwise. Thus, unless expressly stated otherwise, each feature disclosed is one example only of a generic series of equivalent or similar features.

The invention claimed is:

1. An injection device comprising:
   an outer housing configured to receive a syringe, the syringe having a barrel for containing a medicament and a needle in fluid communication with the barrel;
   a needle shield axially moveable relative to the outer housing between a needle covering position and a needle exposing position to selectively provide a needle enclosure, the needle exposing position being axially rearward of the needle covering position;
   a biasing means for biasing the needle shield axially forwardly toward the needle covering position;
   a locking means; and
   a locking sleeve axially movable relative to the outer housing between a non-locking position and a locking position, the locking position being axially rearward of the non-locking position, in which axial movement of the locking sleeve is selectively limited by the locking means;
   wherein in a first configuration, the needle shield is in the needle covering position and the locking sleeve is in the non-locking position so that at least a portion of the needle shield is axially slideable within the locking sleeve to permit rearward axial movement of the needle shield from the needle covering position to the needle exposing position; and
   in a subsequent configuration, the needle shield is in the needle covering position and the locking sleeve is in the locking position so that the needle shield is prevented from moving axially rearwardly by interference with the locking sleeve.

2. The injection device of claim 1, wherein the rearward axial movement of the needle shield from the needle covering position to the needle exposing position causes axial movement of the locking sleeve from the non-locking position to the locking position.

3. The injection device of claim 1, wherein the injection device further comprises a syringe carrier for supporting the syringe within the outer housing.

4. The injection device of claim 3, wherein the syringe carrier is axially moveable relative to the outer housing.

5. The injection device of claim 3, wherein the injection device further comprises a syringe plug which cooperates with the syringe carrier to retain the syringe within the syringe carrier such that the syringe cannot move axially relative to the syringe carrier and the syringe plug.

6. The injection device of claim 5, wherein the syringe plug has an axially extending spigot for insertion into the barrel of the syringe to form a sealing fit between the spigot and an inside of the barrel.

7. The injection device of claim 5, wherein the syringe plug has a channel passing therethrough in fluid communication with the inside of the barrel of the syringe.

8. The injection device of claim 1, wherein the locking means comprises at least one radial protrusion having a corresponding opening in which the radial protrusion is selectively received in order to lock the locking sleeve in the locking position.

9. The injection device of claim 8, wherein the at least one radial protrusion is formed as a part of the locking sleeve and the corresponding opening is formed as a part of the outer housing, or vice versa, thereby preventing a forward axial movement of the locking sleeve relative to the outer housing when the locking sleeve is in the locking position.

10. The injection device of claim 8, wherein the at least one radial protrusion is provided at a free end of a flexible finger to permit radial displacement of the at least one radial protrusion.

11. The injection device of claim 1, wherein the needle shield comprises at least one radial protrusion selectively engageable with the locking sleeve to prevent the needle shield from moving axially rearwardly relative to the locking sleeve when the locking sleeve is in the locking position.

12. The injection device of claim 11, wherein the needle shield further comprises at least one radially flexible arm having a free end upon which the at least one radial protrusion of the needle shield is provided.

13. The injection device of claim 12, wherein the at least one radially flexible arm of the needle shield forms a portion of the needle shield received within the locking sleeve.

14. The injection device of claim 11, wherein in the first configuration, the at least one radial protrusion of the needle shield is axially rearward of a forward facing abutment surface of the locking sleeve.

15. The injection device of claim 11, wherein in the subsequent configuration, the at least one radial protrusion of the needle shield is axially forward of, and at least partially axially aligned with, a forward facing abutment surface of the locking sleeve such that the at least one radial protrusion of the needle shield cannot move axially rearwardly of the forward facing abutment surface of the locking sleeve.

16. The injection device of claim 11, wherein the at least one radial protrusion of the needle shield is radially movable between a first radial position and a second radial position in order to selectively move at least one of the group consisting of into and out of axial alignment with a forward facing abutment surface of the locking sleeve, thereby permitting the at least one radial protrusion of the needle shield to move axially forward of the forward facing abutment surface of the locking sleeve.

17. The injection device of claim 16, wherein the second radial position of the at least one radial protrusion of the needle shield is radially inward of the first radial position of the at least one radial protrusion of the needle shield.

18. The injection device of claim 1, wherein the locking sleeve comprises at least one radial protrusion selectively engageable with the needle shield to inhibit the needle shield from moving axially rearwardly relative to the locking sleeve when the locking sleeve is in the locking position.

19. The injection device of claim 18, wherein the locking sleeve further comprises at least one radially flexible arm having a free end upon which the at least one radial protrusion of the locking sleeve is provided.

20. The injection device of claim 18, wherein in the first configuration, the at least one radial protrusion of the locking sleeve is axially forward of a rearward facing abutment surface of the needle shield.

21. The injection device of claim 18, wherein in the subsequent configuration, the at least one radial protrusion of the locking sleeve is axially rearward of, and at least partially axially aligned with, a rearward facing abutment surface of the needle shield such that the at least one radial protrusion of the locking sleeve cannot move axially forward of the rearward facing abutment surface of the needle shield.

22. The injection device of claim 18, wherein the at least one radial protrusion of the locking sleeve is radially movable between a first radial position and a second radial position in order to selectively move at least one of the group consisting of into and out of axial alignment with a rearward facing abutment surface of the needle shield, thereby permitting the at least one radial protrusion of the locking sleeve to move axially rearward of the rearward facing abutment surface of the needle shield.

23. The injection device of claim 22, wherein the second radial position of the at least one radial protrusion of the needle shield is radially inward of the first radial position of the at least one radial protrusion of the locking sleeve.

\* \* \* \* \*